(12) United States Patent
Al-Ali et al.

(10) Patent No.: US 8,721,542 B2
(45) Date of Patent: May 13, 2014

(54) PHYSIOLOGICAL PARAMETER SYSTEM

(75) Inventors: Ammar Al-Ali, Tustin, CA (US); John Graybeal, Grantville, PA (US); Massi E. Kiani, Laguna Niguel, CA (US); Michael Petterson, Dana Point, CA (US)

(73) Assignee: Masimo Corporation, Irvine, CA (US)

( * ) Notice: Subject to any disclaimer, the term of this patent is extended or adjusted under 35 U.S.C. 154(b) by 1147 days.

(21) Appl. No.: 12/188,154

(22) Filed: Aug. 7, 2008

(65) Prior Publication Data

US 2008/0300471 A1 Dec. 4, 2008

Related U.S. Application Data

(63) Continuation of application No. 11/075,389, filed on Mar. 8, 2005, now Pat. No. 7,415,297.

(60) Provisional application No. 60/551,165, filed on Mar. 8, 2004, provisional application No. 60/600,640, filed on Aug. 11, 2004.

(51) Int. Cl.
*A61B 5/00* (2006.01)
(52) U.S. Cl.
CPC .............. *A61B 5/7275* (2013.01); *A61B 5/746* (2013.01)
USPC ........................... 600/301; 600/323; 600/324
(58) Field of Classification Search
None
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,123,420 A * | 6/1992 | Paret | 600/511 |
| 5,163,438 A | 11/1992 | Gordon et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |

(Continued)

FOREIGN PATENT DOCUMENTS

| | | |
|---|---|---|
| WO | WO 98/10699 | 3/1998 |
| WO | WO 03/053503 A1 | 7/2003 |

OTHER PUBLICATIONS

Bloom, Marc J., "Techniques to Identify Clinical Contexts During Automated Data Analysis", International Journal of Clinical Monitoring and Computing Netherlands, Feb. 1993, vol. 10, No. 1, pp. 17-22.

(Continued)

*Primary Examiner* — Bill Thomson
*Assistant Examiner* — Shirley Jian
(74) *Attorney, Agent, or Firm* — Knobbe Martens Olson & Bear LLP

(57) ABSTRACT

A physiological parameter system has one or more parameter inputs responsive to one or more physiological sensors. The physiological parameter system may also have quality indicators relating to confidence in the parameter inputs. A processor is adapted to combine the parameter inputs, quality indicators and predetermined limits for the parameters inputs and quality indicators so as to generate alarm outputs or control outputs or both.

10 Claims, 8 Drawing Sheets

(56) References Cited

U.S. PATENT DOCUMENTS

| | | |
|---|---|---|
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,337,629 B1 | 1/2002 | Bader |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |

(56) References Cited

U.S. PATENT DOCUMENTS

| | | |
|---|---|---|
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 8,401,607 B2 * | 3/2013 | Mannheimer ............ 600/323 |
| 2002/0190863 A1 | 12/2002 | Lynn |
| 2003/0158466 A1 * | 8/2003 | Lynn et al. ............ 600/300 |
| 2004/0127792 A1 * | 7/2004 | Siejko et al. ............ 600/439 |

OTHER PUBLICATIONS

Horn, Werner, et al. "Effective Data Validation of High-Frequency Data: Time-Point-, Time-Interval-, and Trend-Based Methods", Computers in Biology and Medicine, Sep. 1997, vol. 27, No. 5, pp. 389-409.

EPO Examination Report, dated Sep. 29, 2010 re Application No. 05 724 991.4-1265.

* cited by examiner

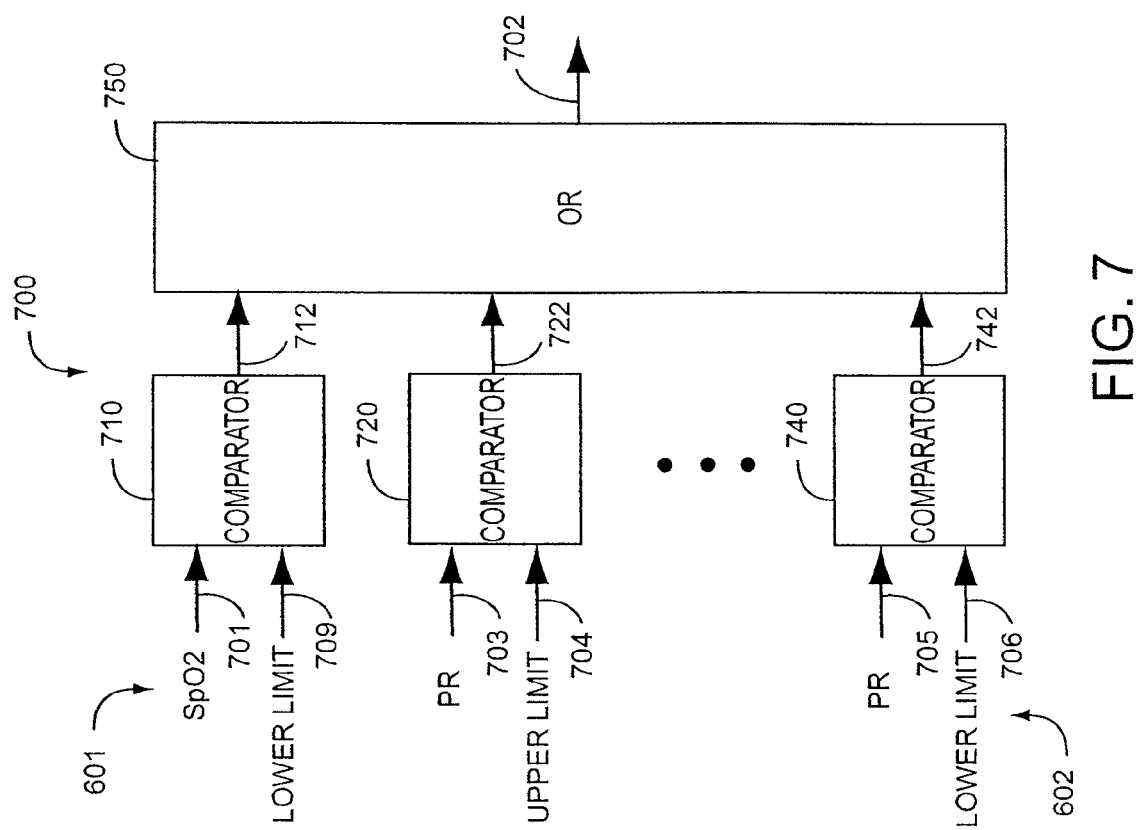

PHYSIOLOGICAL PARAMETER SYSTEM

CROSS-REFERENCE TO RELATED APPLICATIONS

This application is a continuation of U.S. patent application Ser. No. 11/075,389 titled Physiological Parameter System, filed Mar. 8, 2005, which relates to and claims the benefit of U.S. Provisional Applications No. 60/551,165 titled Combined Physiological Parameter Monitor, filed Mar. 8, 2004 and No. 60/600,640 titled Physiological Parameter Controller, filed Aug. 11, 2004. Each of the foregoing applications are incorporated by reference herein.

BACKGROUND OF THE INVENTION

Pulse oximetry is a widely accepted noninvasive procedure for measuring the oxygen saturation level of arterial blood, an indicator of a person's oxygen supply. Early detection of a low blood oxygen level is critical in the medical field, for example in critical care and surgical applications, because an insufficient supply of oxygen can result in brain damage and death in a matter of minutes. A typical pulse oximetry system utilizes a sensor applied to a patient's finger. The sensor has an emitter configured with both red and infrared LEDs that project light through the finger to a detector so as to determine the ratio of oxygenated and deoxygenated hemoglobin light absorption. In particular, the detector generates first and second intensity signals responsive to the red and IR wavelengths emitted by the LEDs after absorption by constituents of pulsatile blood flowing within a fleshy medium, such as a finger tip. A pulse oximetry sensor is described in U.S. Pat. No. 6,088,607 titled Low Noise Optical Probe, which is assigned to Masimo Corporation, Irvine, Calif. and incorporated by reference herein.

Capnography comprises the continuous analysis and recording of carbon dioxide concentrations in the respiratory gases of patients. The device used to measure the $CO_2$ concentrations is referred to as a capnometer. $CO_2$ monitoring can be performed on both intubated and non-intubated patients. With non-intubated patients, a nasal cannula is used. Capnography helps to identify situations that can lead to hypoxia if uncorrected. Moreover, it also helps in the swift differential diagnosis of hypoxia before hypoxia can lead to irreversible brain damage. Pulse oximetry is a direct monitor of the oxygenation status of a patient. Capnography, on the other hand, is an indirect monitor that helps in the differential diagnosis of hypoxia so as to enable remedial measures to be taken expeditiously before hypoxia results in an irreversible brain damage.

SUMMARY OF THE INVENTION

Multiple physiological parameters, combined, provide a more powerful patient condition assessment tool than when any physiological parameter is used by itself. For example, a combination of parameters can provide greater confidence if an alarm condition is occurring. More importantly, such a combination can be used to give an early warning of a slowly deteriorating patient condition as compared to any single parameter threshold, which may not indicate such a condition for many minutes. Conditions such as hypovolemia, hypotension, and airway obstruction may develop slowly over time. A physiological parameter system that combines multiple parameters so as to provide an early warning could have a major effect on the morbidity and mortality outcome in such cases.

Further, a greater emphasis has been put on decreasing the pain level of patients on the ward. Accordingly, patients are often given an IV setup that enables the patient to increase the level of analgesia at will. In certain situations, however, the patient's input must be ignored so as to avoid over medication. Complications from over sedation may include hypotension, tachycardia, bradycardia, hypoventilation and apnea. A physiological parameter system that uses pulse oximetry monitoring of $SpO_2$ and pulse rate in conjunction with patient controlled analgesia (PCA) can aid in patient safety. Utilization of conventional pulse oximetry in conjunction with PCA, however, can result in the patient being erroneously denied pain medication. Conventional monitors are susceptible to patient motion, which is likely to increase with rising pain. Further, conventional monitors do not provide an indication of output reliability.

Advanced pulse oximetry is motion tolerant and also provides one or more indications of signal quality of data confidence. These indicators can be used as arbitrators in decision algorithms for adjusting the PCA administration and sedation monitoring. Further, advanced pulse oximetry can provide parameters in addition to oxygen saturation and pulse rate, such as perfusion index (PI). For example hypotension can be assessed by changes in PI, which may be associated with changes in pulse rate. Motion tolerant pulse oximetry is described in U.S. Pat. No. 6,699,194 titled Signal Processing Apparatus and Method; signal quality and data confidence indicators are described in U.S. Pat. No. 6,684,090 titled Pulse Oximetry Data Confidence Indicator, both of which are assigned to Masimo Corporation, Irvine, Calif. and incorporated by reference herein.

One aspect of a physiological parameter system in a first parameter input responsive to a first physiological sensor and a second parameter input responsive to a second physiological sensor. A processor is adapted to combine the parameters and predetermined limits for the parameters so as to generate an alarm output.

Another aspect of a physiological parameter system is a parameter input responsive to a physiological sensor and a quality indicator input relating to confidence in the parameter input. A processor is adapted to combine the parameter input, the quality indicator input and predetermined limits for the parameter input and the quality indicator input so as to generate a control output.

A physiological parameter method comprises the steps of inputting a parameter responsive to a physiological sensor and inputting a quality indicator related to data confidence for the parameter. A control signal is output from the combination of the parameter and the quality indicator. The control signal is adapted to affect the operation of a medical-related device.

BRIEF DESCRIPTION OF THE DRAWINGS

FIGS. 6-7 are block diagrams of a physiological parameter system utilizing pulse oximetry to control patient controlled analgesia (PCA).

DETAILED DESCRIPTION OF THE PREFERRED EMBODIMENTS

Figure 1:
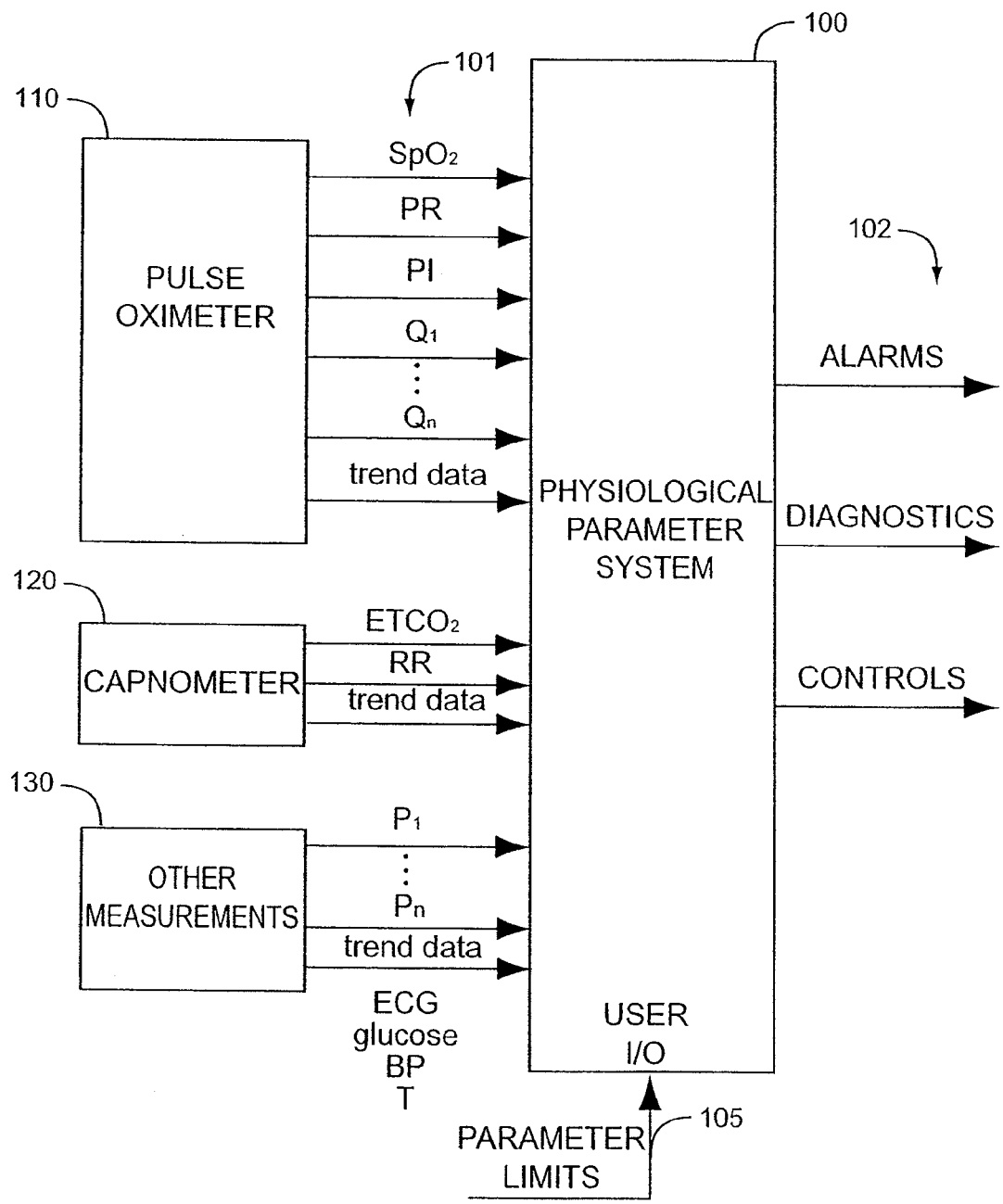
FIG. 1 is a general block diagram of a physiological parameter system having alarm, diagnostic and control outputs.

FIG. 1 illustrates a physiological parameter system 100, which may comprise an expert system, a neural-network or a logic circuit, for example. The physiological parameter system 100 has as inputs 101 one or more parameters from one or more physiological measurement devices, such as a pulse oximetry 110 and/or a capnometer 120. Pulse oximeter parameters may include oxygen saturation ($SpO_2$), perfusion index (PI), pulse rate (PR), various signal quality and/or data confidence indicators (Qn) and trend data, to name a few. Capnography parameter inputs may include, for example, an exhaled carbon dioxide waveform, end tidal carbon dioxide ($ETCO_2$) and respiration rate (RR). Signal quality and data confidence indicators are described in U.S. Pat. No. 6,684,090 cited above. The physiological parameter system 100 may also have parameter limits 105, which may be user inputs, default conditions or otherwise predetermined thresholds within the system 100.

The inputs 101 are processed in combination to generate one or more outputs 102 comprising alarms, diagnostics and controls. Alarms may be used to alert medical personnel to a deteriorating condition in a patient under their care. Diagnostics may be used to assist medical personnel in determining a patient condition. Controls may be used to affect the operation of a medical-related device. Other measurement parameters 130 that can be input to the monitor may include or relate to one or more of ECG, blood glucose, blood pressure (BP), temperature (T), HbCO and MetHb, to name a few.

Figure 2:
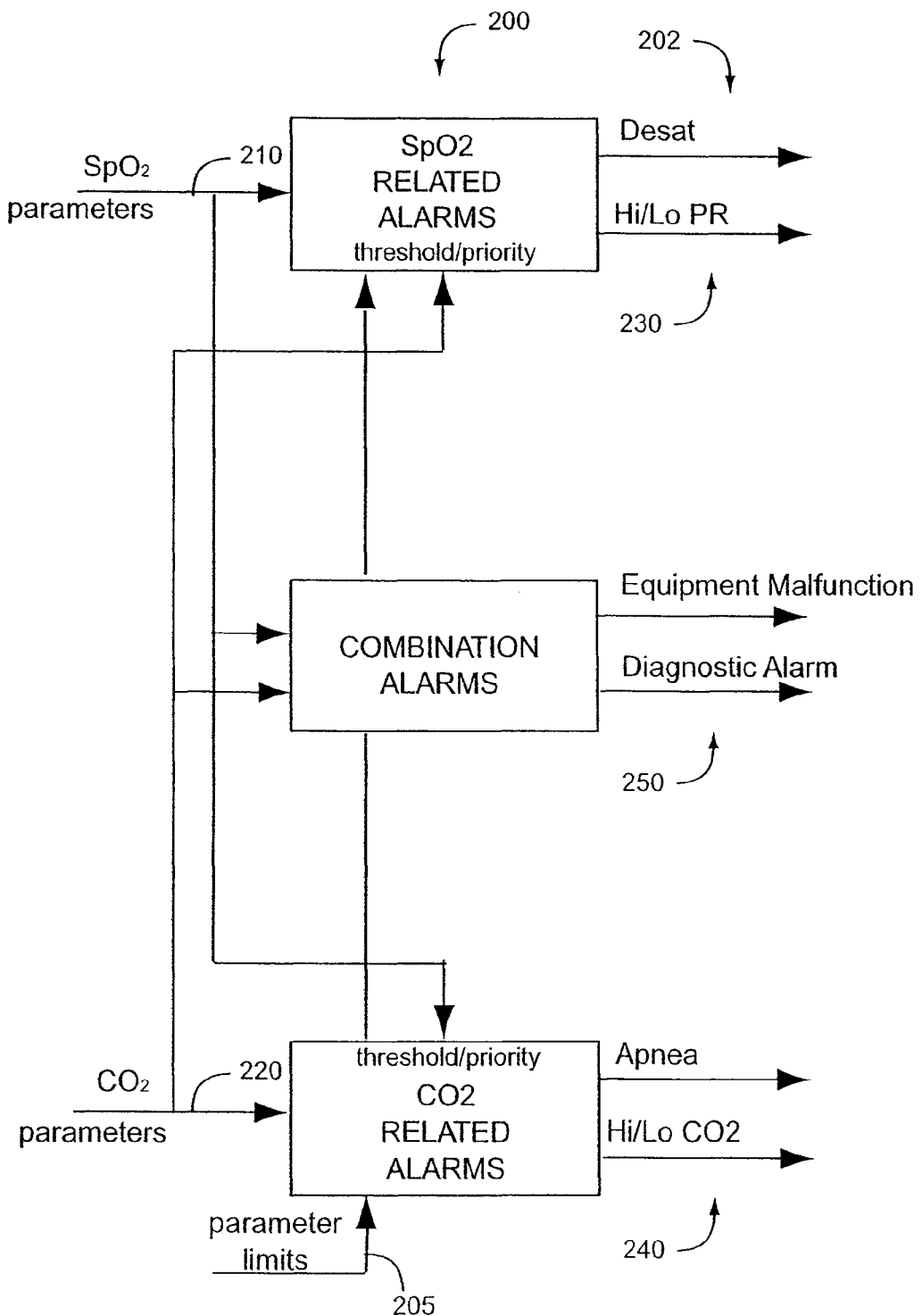
FIG. 2 is a block diagram of a physiological parameter system combining pulse oximetry and capnography and providing alarm outputs.

FIG. 2 illustrates one embodiment of a physiological parameter system 200 combining pulse oximetry parameter inputs 210 and capnography parameter inputs 220 so as to generate alarm outputs 202. Parameter limits 205 may be user inputs, default conditions or otherwise predetermined alarm thresholds for these parameters 210, 220. The alarms 202 are grouped as pulse oximetry related 230, capnography related 240 and a combination 250. For example, a pulse oximetry alarm 230 may be related to percent oxygen saturation and trigger when oxygen saturation falls below a predetermined percentage limit. A capnography alarm 240 may be related to $ETCO_2$ and trigger when $ETCO_2$ falls below or rises above a predetermined mm Hg pressure limit. A combination alarm 250 may indicate a particular medical condition related to both pulse oximetry and capnography or may indicate a malfunction in either instrument.

Figure 3:
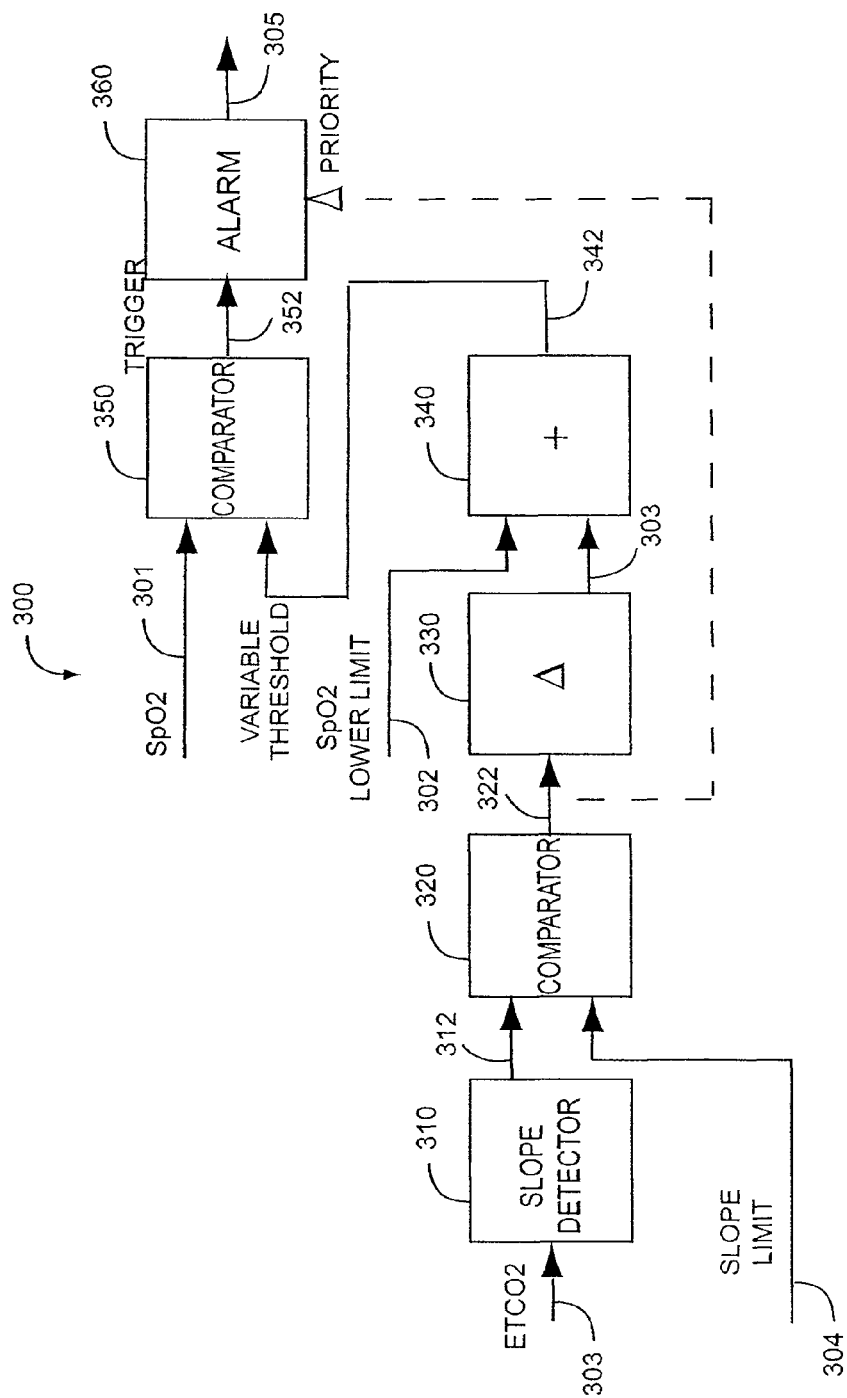
FIG. 3 is a block diagram of a saturation limit alarm enhanced by $ETCO_2$ measurements.

FIG. 3 illustrates a $SpO_2$ alarm embodiment 300 that is responsive to $ETCO_2$. In particular, a $SpO_2$ alarm 305 may be triggered sooner and may indicate a high priority if $ETCO_2$ 303 is falling. That is, if $ETCO_2$ 303 is trending down above a certain rate, the $SpO_2$ alarm 305 is triggered at a higher percentage oxygen saturation threshold and alerts a caregiver to the possibility of a serious condition, e.g., a pulmonary embolism.

As shown in FIG. 3, a slope detector 310 determines the slope 312 of the $ETCO_2$ input 303. A slope comparator 320 compares this slope 312 to a predetermined slope limit 304. If the downward trend of $ETCO_2$ 303 is great enough, a delta value 303 is added 340 to the $SpO_2$ lower limit 302 to generate a variable threshold 342. A threshold comparator 350 compares this variable threshold 342 to the $SpO_2$ input 301 to generate a trigger 352 for the $SpO_2$ alarm 305. The alarm volume, modulation or tone may be altered to indicate priority, based upon the slope comparator output 322.

Figure 4:
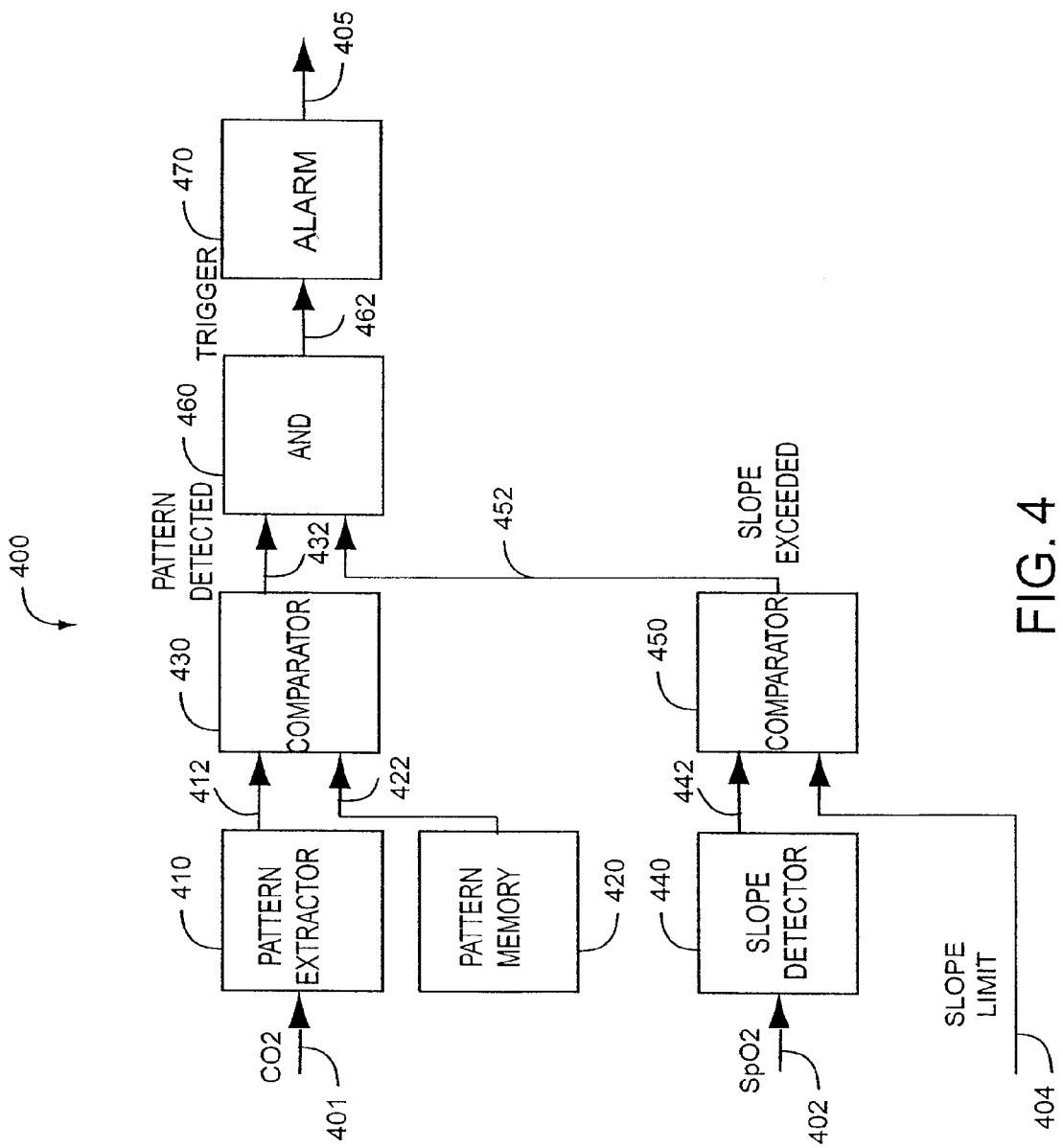
FIG. 4 is a block diagram of a $CO_2$ waveform alarm enhanced by $SpO_2$ measurements.

FIG. 4 illustrates a $CO_2$ alarm embodiment 400 that is responsive to $SpO_2$. In particular, morphology of the input $CO_2$ waveform 401 is utilized to trigger an alarm 405, and that alarm is also responsive to a falling $SpO_2$ 402. That is, if a pattern in the expired $CO_2$ waveform is detected and $SpO_2$ is trending down above a certain rate, then an alarm is triggered. For example, an increasing slope of the $CO_2$ plateau in combination with a downward trend of $SpO_2$ may trigger an alarm and alert a caregiver to the possibility of an airway obstruction.

As shown in FIG. 4, a pattern extractor 410 identifies salient features in the $CO_2$ waveform and generates a corresponding feature output 412. A pattern memory 420 stores one or more sets of predetermined waveform features to detect in the $CO_2$ input 401. The pattern memory 420 is accessed to provide a feature template 422. A feature comparator 430 compares the feature output 412 with the feature template 422 and generates a match output 432 indicating that a specific shape or pattern has been detected in the $CO_2$ waveform 401. In addition, a slope detector 400 determines the slope 442 of the $SpO_2$ input 402. A slope comparator 450 compares this slope 442 to a predetermined slope limit 404. If the downward trend of $SpO_2$ 402 is great enough, a slope exceeded output 452 is generated. If both the match output 432 and the slope exceeded output 452 are each asserted or "true," then a logical AND 460 generates a trigger output 462 to the alarm 470, which generates an alarm output 405.

Figure 5:
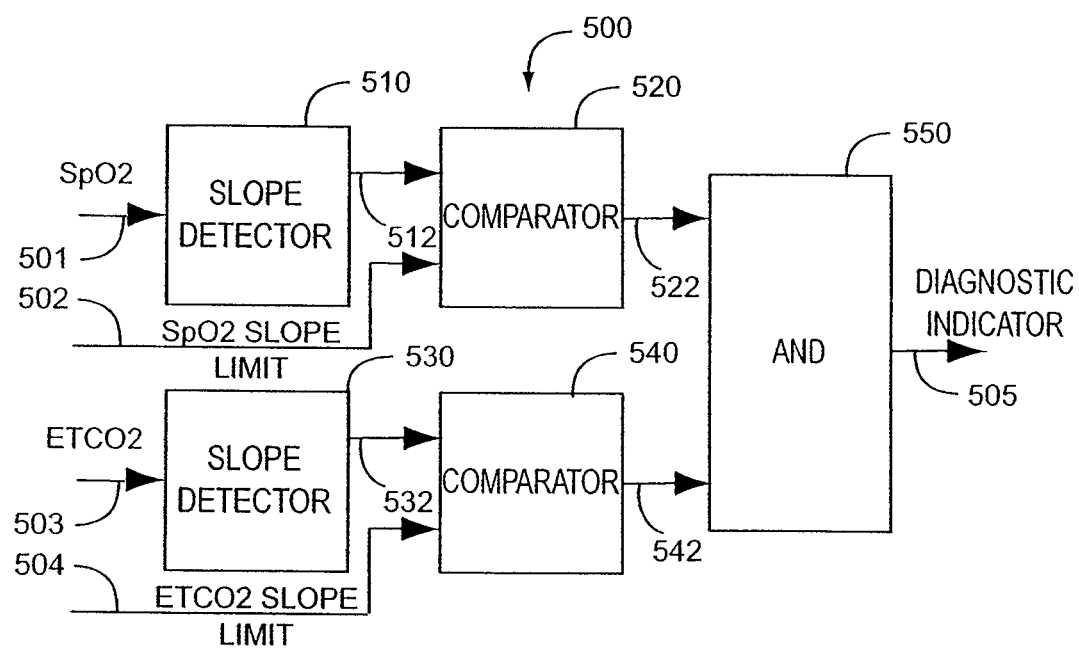
FIG. 5 is a block diagram of a physiological parameter system combining pulse oximetry and capnography and providing a diagnostic output.

FIG. 5 illustrates a combination embodiment 500 having a diagnostic output 505 responsive to both $SpO_2$ 501 and $ETCO_2$ 503 inputs. A $SpO_2$ slope detector 510 determines the slope 512 of the $SpO_2$ input 501 and can be made responsive to a negative slope, a positive slope or s slope absolute value. A first comparator 520 compares this slope 512 to a predetermined $SpO_2$ slope limit 502. If the trend of $SpO_2$ 501 is great enough, a $SpO_2$ slope exceeded output 522 is asserted. Likewise, an $ETCO_2$ slope detector 530 determines the slope 532 of the $ETCO_2$ input 503. A second comparator 540 compares this slope 532 to a predetermined $ETCO_2$ slope limit 504. If the downward trend of $ETCO_2$ 501 is great enough, an $ETCO_2$ slope exceeded output 542 is asserted. If both slope exceeded outputs 522, 542 are asserted or "true," a diagnostic output 505 is asserted.

In one embodiment, the slope detectors 510, 530 are responsive to a negative trend in the $SpO_2$ 501 and $ETCO_2$ 503 inputs, respectively. Accordingly, the diagnostic output 505 indicates a potential embolism or cardiac arrest. In another embodiment, the $SpO_2$ slope detector 510 is responsive to negative trends in the $SpO_2$ 501 input, and the $ETCO_2$ slope detector 530 is responsive to a positive trend in the $ETCO_2$ 503 input. Accordingly, the diagnostic output 505 indicates a potential airway obstruction. The diagnostic output 505 can trigger an alarm, initiate a display, or signal a nursing station, to name a few.

Figure 6A:
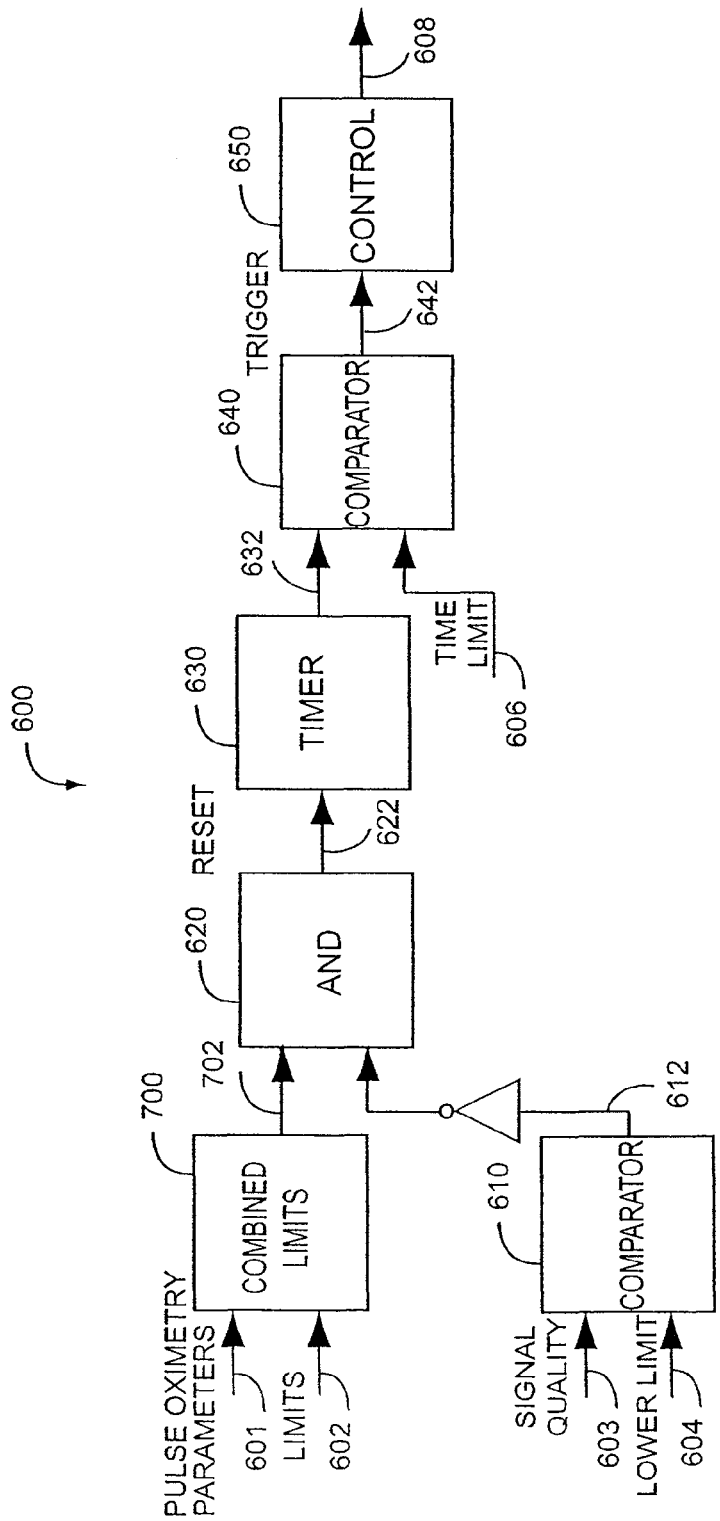
Figure 6B:
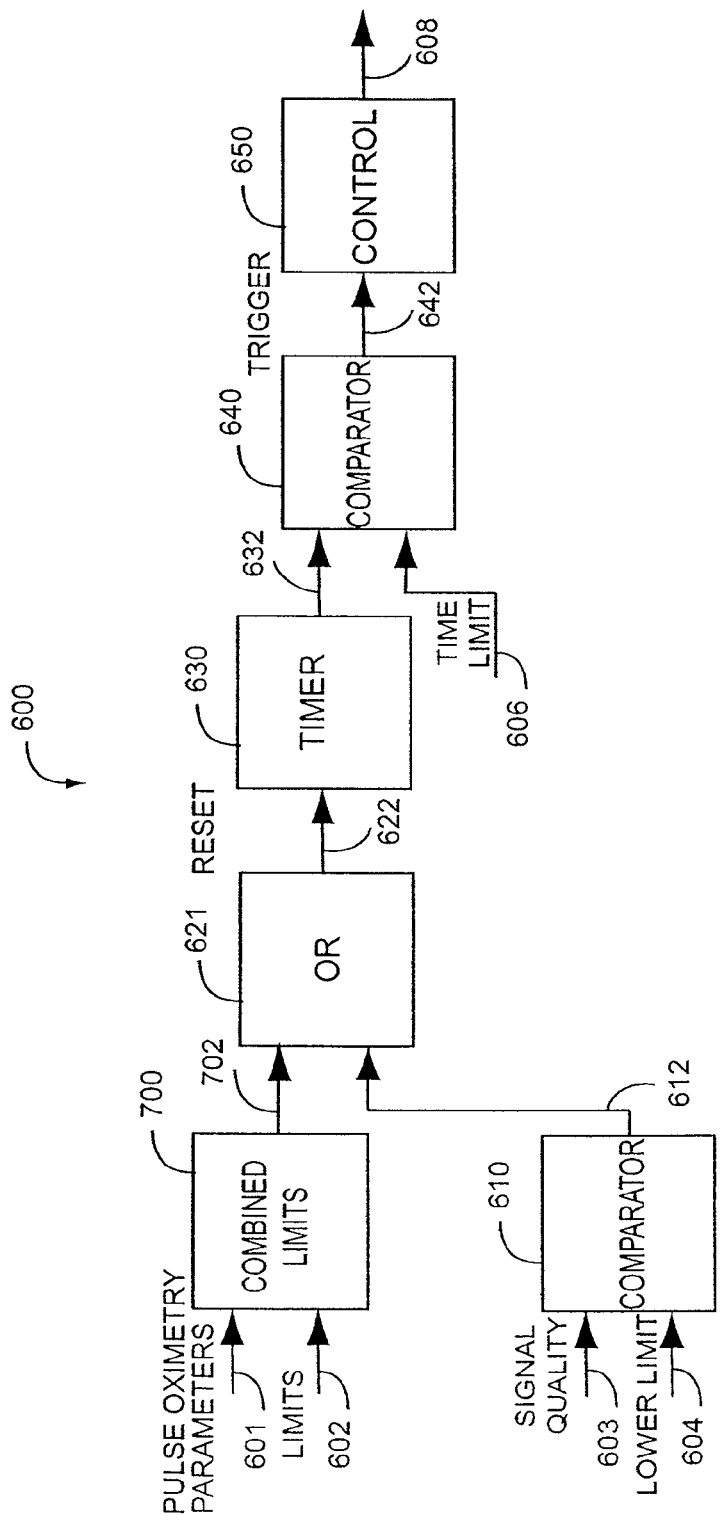

FIGS. 6A-B illustrate a physiological parameter system 600 utilizing pulse oximetry to control patient controlled analgesia (PCA). In particular embodiments, a control output 608 is responsive to pulse oximetry parameters 601 only if signal quality 603 is above a predetermined threshold 604. In FIG. 6A, the control output 608 can be used to lock-out patient controlled analgesia (PCA) if pulse oximetry parameter limits have been exceeded. If signal quality is so low that those parameters are unreliable, however, PCA is advantageously allowed. That is, the pulse oximetry parameters are not allowed to lock-out PCA if those parameters are unreliable. By contrast, in FIG. 6B, the control output 608 can be used to advantageously lock-out or disable patient controlled analgesia (PCA) if pulse oximetry parameter limits have been exceeded or if signal quality is so low that those parameters are unreliable.

As shown in FIG. 6A, pulse oximetry parameters 601 and corresponding limits 602 for those parameters are one set of inputs and a signal quality measures 603 and a corresponding lower limit 604 for signal quality are another set of inputs. The parameters 601 and corresponding limits 602 generate a combined output 703 that is asserted if any of the pulse oximetry parameter limits are exceeded. A comparator 610 compares the signal quality 603 input with a lower limit 604 generating a quality output 612 that is asserted if the signal quality 603 drops below that limit 604. An AND logic 620 generates a reset 622 if the combined output 702 is asserted and the quality output 612 is not asserted. The reset 622 resets the timer 630 to zero. A comparator 640 compares the timer output 632 to a predetermined time limit 606 and generates a trigger 642 if the time limit is exceeded. The trigger 642 causes the control 650 to generate the control output 608, enabling a patient controlled analgesia (PCA), for example. In this manner, the PCA is enabled if all monitored parameters are within set limits and signal quality is above its lower limit for a predetermined period of time.

As shown in FIG. 6B, the combined output 702, quality output 612, reset 622, timer 630, comparator 640 and control 650 are generated as described with respect to FIG. 6A, above. An OR logic 621 generates a rest 622 if either the combined output 702 or the quality output 612 is asserted. In this manner, the PCA is disabled for a predetermined period of time if any of the monitored parameters are outside of set limits or the signal quality is below its lower limit.

FIG. 7 illustrates combined limits 700 having $SpO_2$ parameters 601 and corresponding thresholds 602 as inputs and providing a combination output 702. In particular, if any parameter 601 exceeds its corresponding limit 602, the output of the corresponding comparator 710, 720, 740 is asserted. An OR logic 750 is responsive to any asserted output 712, 722, 742 to asserted the combined output 702. For example, the combined output 702 may be asserted if $SpO_2$ 701 falls below a lower limit 709, pulse rate (PR) 703 rises above an upper limit 704 or PR 703 falls below a lower limit 706.

A physiological parameter system has been disclosed in detail in connection with various embodiments. These embodiments are disclosed by way of examples only and are not to limit the scope of the claims that follow. One of ordinary skill in the art will appreciate many variations and modifications. For example, the control output 608 (FIG. 6B) can be used to control (titrate) delivered, inspired oxygen levels to patients based upon pulse oximetry parameters, unless signal quality is so low that those parameters are unreliable. One of ordinary skill in the art will also recognize that the control output 608 (FIG. 6B) can be used to control patient delivery of any of various pharmacological agents and/or medical gases.

What is claimed is:

1. A patient monitor comprising:
   a first input configured to receive a first parameter signal, said first parameter signal indicative of a first physiological parameter of a patient and said first parameter signal responsive to a first physiological sensor monitoring said patient;
   a second input configured to receive a second parameter signal, the second parameter signal indicative of a second physiological parameter of the patient and responsive to a second physiological sensor monitoring said patient, the second physiological parameter different than the first physiological parameter; and
   a processor responsive to a combination of both of said first and second inputs to generate a diagnostic indication of a patient condition or an alarm output, wherein the processor is configured to:
      determine trend data based on the second parameter signal;
      set a variable threshold in response to the trend data;
      determine a measurement reading of first physiological parameter based on the first parameter signal;
      compare the measurement reading of the first physiological parameter to the variable threshold; and
      generate the diagnostic indication or the alarm output based at least in part on said comparison.

2. The patient monitor according to claim 1, wherein said processor is responsive to a predetermined limit related to said trend data of the second parameter signal, wherein said diagnostic indication of a patient condition or alarm output is triggered when said measurement reading of the first physiological parameter is below said variable threshold, and wherein said processor raises said variable threshold in response to said trend data of the second parameter signal and said predetermined limit.

3. The patient monitor according to claim 2 wherein:
said first parameter signal comprises values responsive to an $SpO_2$ of the patient;
said second parameter signal comprises values responsive to an $ETCO_2$ of the patient; and
said variable threshold is a lower limit for the $SpO_2$ that is raised in response to a downward trend in the $ETCO_2$ at a rate greater than said predetermined limit.

4. The patient monitor of claim 1, wherein the first sensor and the second sensor each comprise one or more of a pulse oximetry sensor, a blood pressure sensor, an ECG sensor, an acoustic sensor, or a capnographer.

5. The patient monitor of claim 1, wherein the first physiological sensor monitors said patient at a first measurement site and the second physiological sensor monitors said patient at a second measurement site different from said first measurement site.

6. A method of monitoring a patient using trend data, comprising:
   obtaining a measurement of a first physiological parameter from a first physiological sensor monitoring said patient;
   obtaining a measurement of a second physiological parameter from a second physiological sensor monitoring said patient, said second physiological parameter different than said first physiological parameter; and
   using one or more processors of a physiological monitor:
      determining trend data based on said second physiological parameter measurement;
      setting a variable threshold in response to the trend data;
      comparing said measurement of the first physiological parameter to said variable threshold; and
      generating a diagnostic indication of a patient condition or an alarm output based at least in part on said comparison.

7. The method of claim 6, further comprising:
providing a predetermined limit related to said trend data of the second physiological parameter measurements; and
using said one or more processors of said physiological monitor:
   triggering said diagnostic indication of a patient condition or alarm output when said measurement of the first physiological parameter is below said variable threshold, and raising said variable threshold in response to said trend data and said predetermined limit.

8. The method of claim 7, wherein:
said first physiological parameter measurement comprises values responsive to an $SpO_2$ of the patient;
said second physiological parameter measurement comprises values responsive to an $ETCO_2$ of the patient; and
said variable threshold is a lower limit for the $SpO_2$ that is raised in response to a downward trend in the $ETCO_2$ at a rate greater than said predetermined limit.

9. The method of claim 6, wherein said first physiological sensor and said second physiological sensor each comprise one or more of a pulse oximetry sensor, a blood pressure sensor, an ECG sensor, an acoustic sensor, or a capnographer.

10. The method of claim 6, wherein the first physiological sensor monitors said patient at a first measurement site and the second physiological sensor monitors said patient at a second measurement site different from said first measurement site.

* * * * *

UNITED STATES PATENT AND TRADEMARK OFFICE
CERTIFICATE OF CORRECTION

| | | |
|---|---|---|
| PATENT NO. | : 8,721,542 B2 | Page 1 of 1 |
| APPLICATION NO. | : 12/188154 | |
| DATED | : May 13, 2014 | |
| INVENTOR(S) | : Al-Ali et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1264 days.

Signed and Sealed this
Tenth Day of November, 2015

Michelle K. Lee
*Director of the United States Patent and Trademark Office*